United States Patent [19]
Falchetto et al.

[11] Patent Number: 5,932,762
[45] Date of Patent: *Aug. 3, 1999

[54] PROCESS FOR THE PRODUCTION OF ARYL CYANATES

[75] Inventors: Alessandro Falchetto, Monte Crestese, Italy; Ulrich Daum, Hofstetten, Switzerland

[73] Assignee: Lonza, Ltd., Gampel/Valais, Switzerland

[*] Notice: This patent issued on a continued prosecution application filed under 37 CFR 1.53(d), and is subject to the twenty year patent term provisions of 35 U.S.C. 154(a)(2).

[21] Appl. No.: 08/780,444

[22] Filed: Jan. 8, 1997

Related U.S. Application Data

[63] Continuation-in-part of application No. 08/344,576, Nov. 18, 1994, abandoned.

[30] Foreign Application Priority Data

May 27, 1994 [CH] Switzerland .............................. 1641/94

[51] Int. Cl.$^6$ ................................................. C07C 261/02
[52] U.S. Cl. .............................................................. 560/301
[58] Field of Search ............................................. 560/301

[56] References Cited

U.S. PATENT DOCUMENTS 5,420,342  5/1995  Craig, Jr. ................................. 560/301

FOREIGN PATENT DOCUMENTS

| | | |
|---|---|---|
| 1195764 | 3/1966 | Germany . |
| 1720663 | 9/1975 | Germany . |
| 2507671 | 9/1976 | Germany . |
| 2507705 | 9/1976 | Germany . |
| 2529486 | 1/1977 | Germany . |
| 2529487 | 1/1977 | Germany . |
| 2446004 | 1/1980 | Germany . |

*Primary Examiner*—Robert Gerstl
*Attorney, Agent, or Firm*—Fisher, Christen & Sabol

[57] ABSTRACT

A process for the production of aryl cyanates of the general formula I:

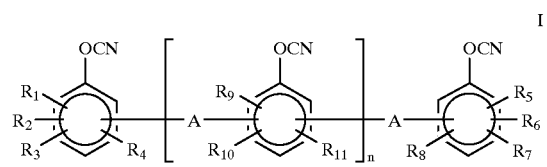

A phenol of the general formula II:

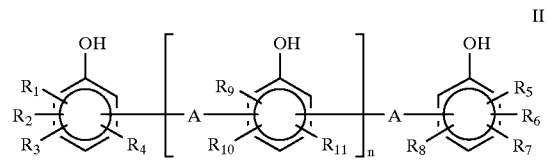

a tertiary amine and cyanogen chloride, of which at least one of the three components is present as a solution in an organic solvent, are fed essentially simultaneously and continuously at a temperature of −20° C. to 0° C. and in a molar ratio of cyanogen chloride to the reactive hydroxy groups of the phenol of 1.0:1.0 to 1.2:1.0 in a cooled loop reactor, so that the reaction components, before they come in contact with one another, are prediluted by the reaction mixture circulating in the loop reactor. Simultaneously, a stream of the reaction mixture corresponding to the fed volume of the reaction components is drawn off from the circulation.

18 Claims, 2 Drawing Sheets

PROCESS FOR THE PRODUCTION OF ARYL CYANATES

This is a continuation-in-part of U.S. application Ser. No. 08/344,576, filed on Nov. 18, 1994 now abandoned.

BACKGROUND OF THE INVENTION

1. Field Of The Invention

The invention relates to a continuous process for the production of multivalent aryl cyanates from the corresponding phenols and cyanogen chloride.

2. Background Art

Aryl cyanates, the phenol esters of cyanic acid, are important building blocks for synthetic resins (see, e.g., German OS 1,720,663). Usually aryl cyanates are produced from the corresponding phenols and cyanogen chloride, and the hydrogen chloride resulting as by-product is bound by a base as a salt (German AS 1,195,764). Since cyanogen chloride can be viewed as chloride of cyanic acid, this reaction formally corresponds to the production of an ester from the corresponding alcohol and the corresponding acid chloride. But since both cyanogen chloride and the resulting aryl cyanates are highly reactive compounds, precisely defined reaction conditions must be maintained for suppression of secondary and subsequent reactions to obtain satisfactory yields and sufficiently pure products. In particular, in the case of such aryl cyanates, which can be purified neither by distillation nor by crystallization, special significance attaches to the last-mentioned criterion.

The known processes for the production of pure multivalent aryl cyanates (German OS 2,446,004; 2,507,671; 2,507,705; 2,529,486 and 2,529,487) are either discontinuous processes or require an aqueous-organic two-phase system. Furthermore, an excess of cyanogen chloride must often be introduced in the discontinuous processes, which in the case of large batches, also represents a safety risk (cyanogen chloride is very toxic).

BROAD DESCRIPTION OF THE INVENTION

The main object of the invention is to provide a continuous process which is suitable for the production of large amounts of highly pure aryl cyanates and which can be performed simply and safely. Other objects and advantages of the invention are set out herein or are obvious herefrom to one skilled in the art.

The objects and advantages of the invention are achieved by the process of the invention.

The invention involves a process for the production of aryl cyanates of the general formula:

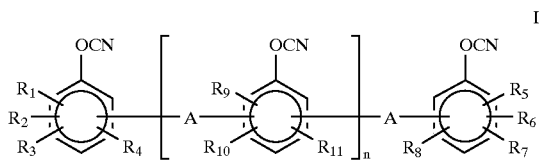

wherein:

(a) n is a whole number from 0 to 20, and A is a direct bond, oxygen, sulfur, sulfonyl, carbonyl, carbonyldioxy, an optionally completely or partially fluorine-substituted, straight-chain or branched $C_1$–$C_{10}$-alkanediyl group, an optionally $C_1$–$C_4$-alkyl- and/or halogen-substituted, divalent monocyclic or polycyclic aromatic radical, an optionally $C_1$–$C_4$-alkylsubstituted, divalent monocyclic or polycyclic cycloaliphatic radical or a divalent group composed of two or more of the above-mentioned groups, and, if n is greater than zero, the groups respectively symbolized by A can be the same or different, or (b) n equals zero, A is a group of formula:

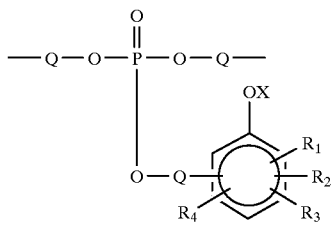

and Q is a direct bond, an optionally completely or partially fluorine-substituted, straight-chain or branched $C_1$–$C_{10}$-alkanediyl group, an optionally $C_1$–$C_4$-alkyl- and/or halogen-substituted, divalent monocyclic or polycyclic aromatic radical or a divalent group composed of two or more of the above-mentioned groups and X is —CN, and $R_1$ to $R_{11}$ are each the same or different and are hydrogen, halogen, $C_1$–$C_4$-alkoxy, $C_1$–$C_4$-alkylthio, $C_1$–$C_4$-alkoxycarbonyl or optionally completely or partially fluorine-substituted $C_1$–$C_4$alkyl, by reaction of phenols of the general formula:

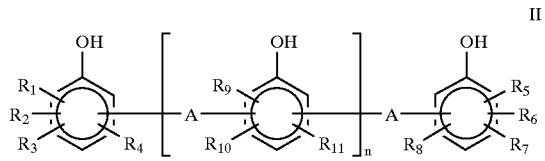

wherein n, A, Q and $R_1$ to $R_{11}$ have the above-mentioned meanings and X is hydrogen, with cyanogen chloride in the presence of a tertiary amine. The phenol, the amine and the cyanogen chloride, of which at least one of the three components is present as a solution in an organic solvent, are fed essentially simultaneously and continuously at a temperature of −20° C. to 0° C. and in a molar ratio of cyanogen chloride to the reactive hydroxy groups of the phenol of 1.0 to 1.2 in a cooled loop reactor, so that the reaction components, before they come in contact with one another, are prediluted by the reaction mixture circulating in the loop reactor, and simultaneously, a stream of the reaction mixture corresponding to the fed volume of the reaction components is drawn off from the circulation.

Preferably the molar ratio of cyanogen chloride to the reactive hydroxyl groups of the phenol is from 1.0:1.0 to 1.1:1.0. Preferably a trialkylamine of formula RR'R"N is used as the tertiary amine, wherein R, R' and R" are the same or different and each is a straight-chain or branched $C_1$–$C_6$-alkyl group. Preferably triethylamine is used as the tertiary amine. Preferably an organic solvent is used, in which the resulting tertiary ammonium chloride is poorly soluble. The tertiary ammonium chloride is separated completely or partially from the reaction mixture by filtration or centrifuging. A solvent is used, which is not water-miscible and the reaction mixture, optionally after filtration or centrifuging, is extracted with water.

DETAILED DESCRIPTION OF THE DRAWINGS

Figure 1:
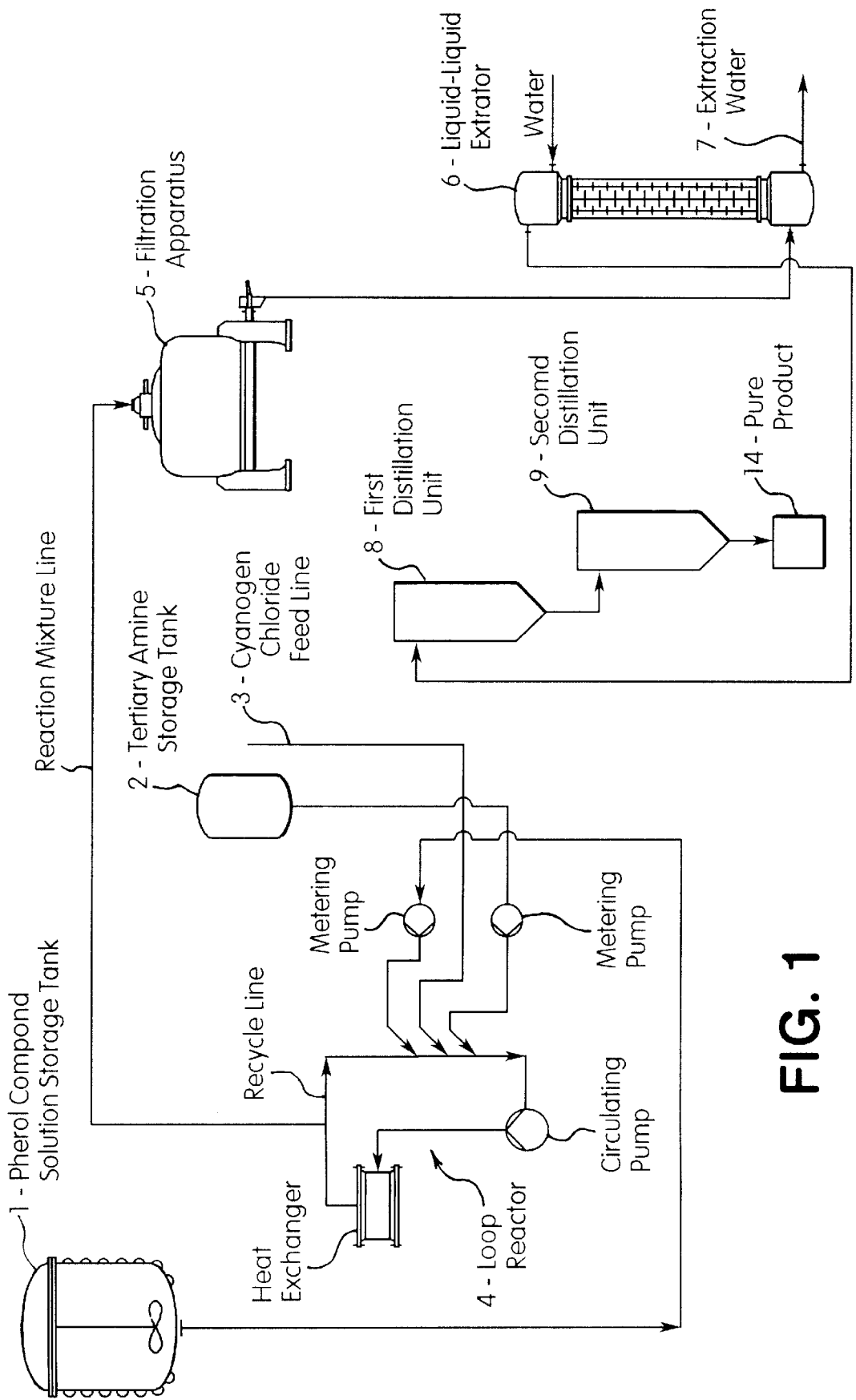
Figure 2:
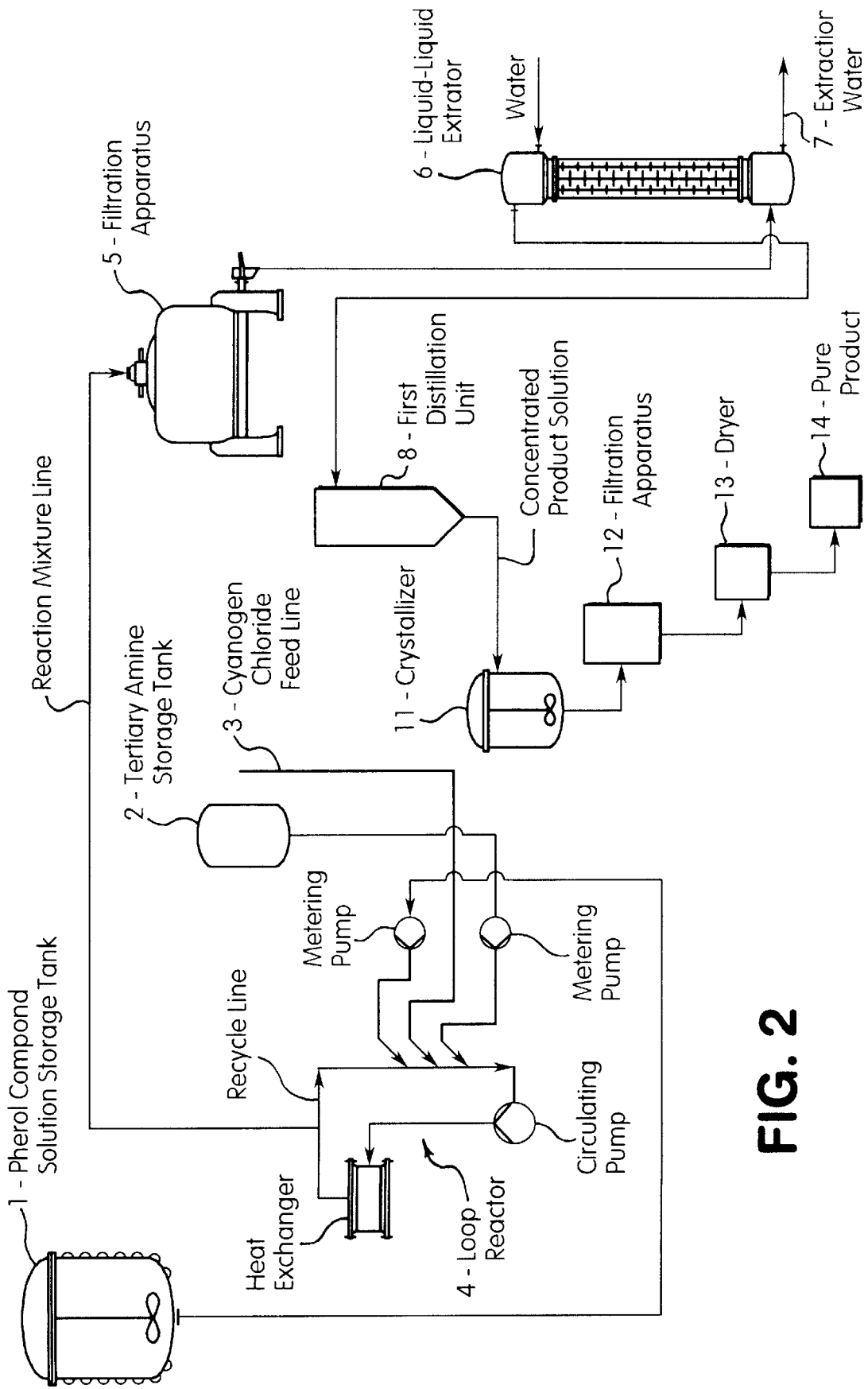

In the drawings;

FIG. 1 is a diagram showing a unit for the production of noncrystalline aryl cyanates; and FIG. 2 is a diagram showing the arrangement for the production of crystalline products.

The diagrammatic drawings (FIGS. 1 and 2) are used as embodiments only to illustrate the main object of the invention, without the invention being limited to the embodiments shown.

FIG. 1 diagrammatically shows a unit for the production of noncrystalline aryl cyanates. From stirred storage tank 1, the phenol solution is fed by a metering pump to reactor loop 4 equipped with a circulating pump and a heat exchanger. Simultaneously to this feeding of the phenol solution, the tertiary amine is fed from storage tank 2 also by a metering pump and the cyanogen chloride is fed by pipe 3. The reaction mixture is guided by a pipe (on top, in FIG. 1) continuously to filtration apparatus 5, and the filtrate is guided from there further to liquid-liquid-extractor 6, where it is extracted in counter current with water. Extraction water 7 is fed to the waste water treatment. The production solution in first distillation unit 8 is freed from the solvent and in second distillation unit 9 from highly volatile by-products and contaminants. Pure product 10 is drawn off from the bottom of second distillation unit 9.

FIG. 2 also diagrammatically shows the arrangement for the production of crystalline products. The reactor part (numbers 1 to 4) and the working-up part up to solvent distillation (numbers 5 to 8) are identical with the arrangement according to FIG. 1. A concentrated product solution is guided into crystallizer 11 from the bottom of solvent distillation unit 8. The crystal mass formed there goes into filtration apparatus 12 and the filter cake from there goes into dryer 13, from which finished product 14 is taken.

The multivalent aryl cyanates that can be produced according to the invention can be described by the general formula:

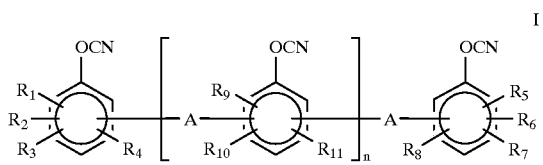

I

Therein, n is a whole number from 0 to 20, preferably 0 to 10. Thus, both divalent and multivalent (oligomeric) aryl cyanates come within formula I. The latter are derived, for example, from multivalent phenols of the Novolak type.

A can be both a direct chemical bond and a divalent group. Examples of the divalent groups are oxygen, sulfur, sulfonyl, carbonyl and carbonyldioxy (—O—C(=O)—O—). Also, examples of the divalent groups are straight-chain or branched $C_1$–$C_{10}$-alkanediyl groups, which optionally can be completely or partially fluorine-substituted, divalent monocyclic or polycyclic aromatic radicals, which optionally can be substituted with one or more $C_1$–$C_4$-alkyl groups and/or one or more halogen atoms, or divalent monocyclic or polycyclic cycloaliphatic radicals, which optionally can be substituted with one or more $C_1$–$C_4$-alkyl groups. Furthermore, A can be a divalent group composed of two or more of the above-mentioned divalent groups. If n is greater than zero and thus several divalent groups A are present, the latter can be the same or different. But preferably the groups A are the same.

If n is equal to zero, A can also be a group of the formula:

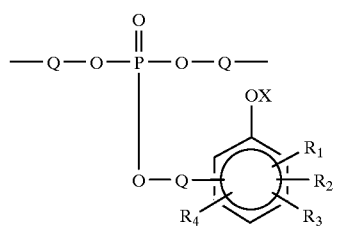

Therein, Q is respectively either a direct bond or a divalent group. Examples of the divalent groups are straight-chain or branched $C_1$–$C_{10}$-alkanediyl groups, which optionally can be completely or partially fluorine-substituted, divalent monocyclic or polycyclic aromatic radicals, which optionally can be substituted with one or more $C_1$–$C_4$-alkyl groups and/or one or more halogen atoms, or divalent groups, which are composed of two or more of the above-mentioned groups. In this case, X is —CN.

The aromatic rings carrying the cyanate groups can also carry substituents $R_1$ to $R_{11}$ on the "free" carbon atoms. Substituents $R_1$ to $R_{11}$ can be the same or different and, in addition to hydrogen, are respectively halogen, $C_1$–$C_4$-alkoxy, $C_1$–$C_4$-alkylthio, $C_1$–$C_4$-alkoxycarbonyl or $C_1$–$C_4$-alkyl which optionally can be completely or partially fluorine-substituted.

Both divalent groups A and Q and substituents $R_1$ to $R_{11}$ can respectively be in ortho-, meta- or para-position to the cyanate groups, and the substitution pattern on the individual aromatic rings can be the same or different both within a molecule and from molecule to molecule.

The term "alkanediyl group" is here and below both those groups whose free valences start from the same carbon atom, such as, methylene, ethylidene or 1-methylethylidene (=isopropylidene) and those whose free valences start from different carbon atoms, such as, 1,2-ethanediyl (=ethylene) or 1,3-propanediyl (=trimethylene).

An example for a fluorine-substituted alkanediyl group is 1-(trifluoromethyl)-2,2,2-trifluoroethylidene.

The term "polycyclic" is here and below all cyclic structures, which exhibit at least two rings. This includes singly connected rings, such as, biphenyl, spiro compounds, condensed ring systems, such as, naphthalene, or bridged ring systems, such as, norbornane.

Divalent aromatic radicals are, for example, o-, m- and p-phenylene and the various isomeric naphthalenes and biphenylenes.

In divalent cycloaliphatic radicals, the two free valences can start from the same carbon atom, such as, in cyclohexylidene, or from different carbon atoms, such as, in octahydro-4,7-methano-indene-diyl.

Composite divalent groups are, for example, those of the formulas:

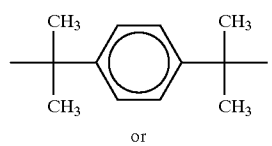

or

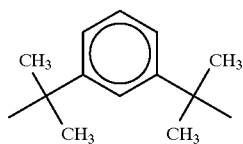

According to the invention, the multivalent aryl cyanates are produced from the corresponding multivalent phenols of the general formula:

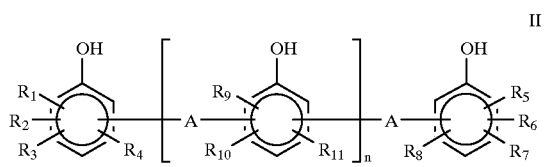

and cyanogen chloride in the presence of a tertiary amine.

Index n as well as groups A, $R_1$ to $R_{11}$ and, if present, Q have herein the same meanings as in product (I), while X, if present, stands for hydrogen.

According to the invention, the three components are brought to reaction with one another in a cooled loop reactor. The term "loop reactor" in this case does not stand for a specific design, but only for the operating principle. In the simplest case, the loop reactor consists of a ring-shaped, closed tube (loop), in which a circulating pump is incorporated. The cooling necessary because of the exothermicity of the reaction and the low reaction temperature can be achieved, for example, by a cooling jacket extending over an essential part of the tube length or a heat exchanger of usual design incorporated at any point in the loop. At least one connection to draw off the reaction mixture and several, preferably three, connections to feed the reaction components are present on the loop.

Since the reaction of phenol (II) with the cyanogen chloride occurs in solution, at least one of the three components to be fed must be present in dissolved form. In general, the phenol is used as a solution in an organic solvent, since phenols are normally solid at the reaction temperature. Of course, the cyanogen chloride and/or the tertiary amine can also be added in dissolved or diluted form.

The feeding of the reaction components to the loop reactor takes place essentially simultaneously and continuously. This means that no prolonged interruptions or strong fluctuations of the molar ratio of the reaction components in the reaction mixture occur. But slight fluctuations, as they can occur, for example, by pulsations of piston pumps or diaphragm pumps, are permissible.

The feeding of the reaction components to the loop reactor further takes place so that the latter first come in contact with one another after dilution by the circulating reaction mixture. This is achieved by corresponding arrangement of the feeding points taking into consideration the flow conditions in the loop. But it is not necessary to force an ideal mixing.

The volume ratio of the circulating stream in the loop reactor to the combined feed stream of the reaction components is preferably at least about 10:1, respectively, and is most preferably equal to or greater than about 100:1, respectively.

Simultaneously with the feeding of the reaction components, a stream of the reaction mixture corresponding to the fed volume is drawn off from the loop reactor and fed to the working-up. If the loop, as usual, is constantly completely filled, this condition is automatically met.

The reaction temperature is suitably −20° C. to 0° C., and the fed reaction components are advantageously precooled. If the cyanogen chloride is fed in pure form, thus not as solution, the narrow liquid range (−6° C. to +14° C.) of this substance is to be taken into consideration.

The molar ratio of cyanogen chloride to the reactive hydroxy groups of the phenol is suitably 1.0:1.0 to 1.2:1.0 and preferably 1.0:1.0 to 1.1:1.0. These values relate to the fed amounts, the ratios actually present in the reaction mixture can vary more or less greatly from them.

As the tertiary amine, a trialkylamine of the general formula RR'R"N is advantageously used, in which R, R' and R" can be the same or different and each is a straight-chain or branched $C_1$–$C_6$-alkyl group. Especially preferred is triethylamine.

As the solvent for performing the reaction, basically every organic solvent can be used, in which the reaction components are sufficiently soluble and which does not react with cyanogen chloride or another of the components. For this purpose, especially esters, such as, ethyl acetate or butyl acetate, ethers, such as, tetrahydrofuran, ketones, such as, acetone or halogenated hydrocarbons, such as, dichloromethane, are suitable.

For the working-up, it is advantageous to use a solvent, in which the product is soluble, but the tertiary ammonium chloride resulting as by-product is not or only poorly soluble. The latter then precipitates and can be completely or partially separated by filtration or centrifuging.

The reaction and working-up can be performed in different solvents, by, for example, the solvent of the reaction mixture drawn off from the loop reactor being distilled off and replaced by another solvent.

Further, it can be advantageous to use a solvent, which is not or only slightly water-miscible, and to extract with water the reaction mixture to remove the tertiary ammonium chloride. This is especially important in the production of those aryl cyanates that can be purified neither by crystallization nor by distillation.

The further working-up takes place according to methods known in the art and depends essentially on the physical properties of the individual products.

After concentrating the solution, products that can be crystallized are advantageously crystallized, filtered or centrifuged and finally dried.

In the products that cannot be crystallized, the solvent is first completely distilled off and then highly volatile by-products are optionally separated in a second distillation.

The process according to the invention is suitable, for example, for the production of the following compounds:

4,4'-thiodiphenylcyanate of the formula:

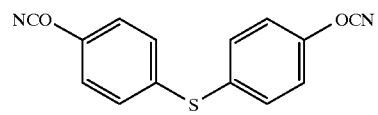

4,4'-methylene-bis(2,6-dimethylphenylcyanate) of the formula:

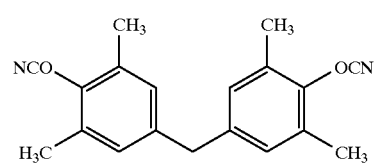

aryl cyanate of the formula:

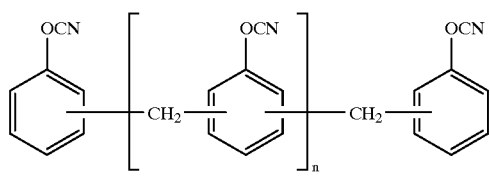

4,4'-ethylidenediphenylcyanate of the formula:

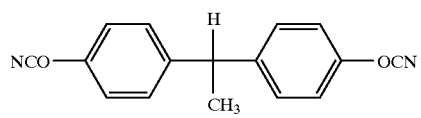

2,2-bis(4-cyanatophenyl)propane of the formula:

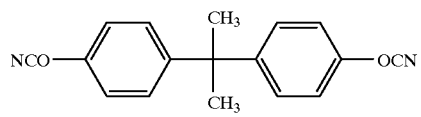

4,4'-bis(trifluoromethyl)methylenediphenylcyanate of the formula:

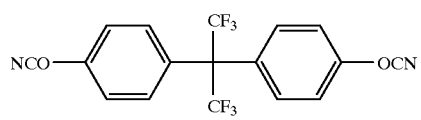

aryl cyanate of the formula:

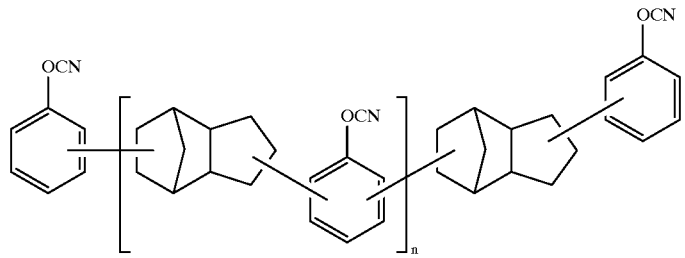

4,4'-(1,3-phenylenediisopropylidene)diphenylcyanate of the formula:

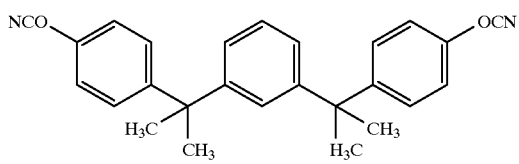

phosphoric acid tri[4-(1-[4-cyanatophenyl]-1-methylethyl)phenylester] of the formula:

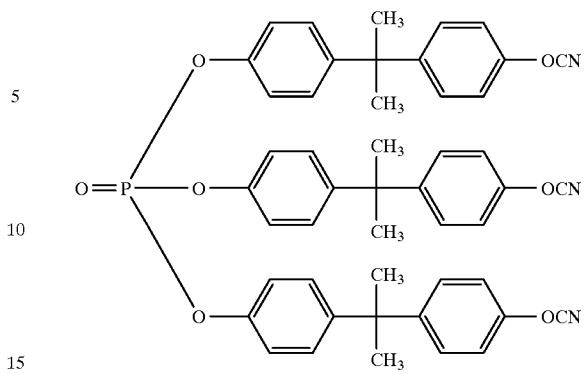

EXAMPLE 1

Production of 2,2-bis (4-cyanatophenyl) propane (Bisphenol A-dicyanate)

In a loop reactor of 15 l volume cooled to a −10° C. inside temperature, 100 kg/h of a 15 percent solution of bisphenol A in acetone and 13.6 kg/h of triethylamine were metered by metering pumps simultaneously and separately from one another. At the same time, 8.5 kg/h of cyanogen chloride (corresponding to a molar ratio of 1:1.02:1.05) was introduced. The reaction mixture was circulated by a circulating pump in the loop and overflowed into a collecting tank. The circulating pump delivered a circulating stream of about 11,000 l/h, which corresponded to a volume ratio of the circulating stream to the combined feed stream of about 100:1. There, it was first stirred, to prevent a sedimentation of the precipitated triethylammonium chloride, and added batchwise to a nutsche filter. The filter cake was washed with acetone and further processed for recovery of the triethylamine. The filtrate was concentrated by evaporation, and about 80 percent of the solvent was distilled off. The concentrated product solution thus obtained with a temperature of 60° C. to 70° C. was introduced with vigorous stirring in water of about 10° C. The precipitated product was centrifuged off, washed twice with water and dried in a paddle dryer at 50° C. and about 50 mbars for 24 hours. The purity of the end product was 97.5 to 99.5 percent, and the yield (relative to bisphenol A) was about 90 percent.

EXAMPLE 2
Production of Novolac Cyanate

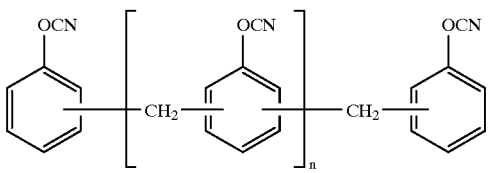

Into a 15 l loop reactor that was cooled to an internal temperature of −7° to −3° C., 90 l/h of a solution of 60 kg of novolac (DURITE®) 333A, Borden Chemicals), that was precooled to −10° C., and 62.4 kg of triethylamine in 256.2 l of dichloromethane were introduced via a metering pump, and 10 kg/h of cyanogen chloride was simultaneously introduced via a control valve. The reaction mixture was circulated in the loop by a circulating pump at a pressure of 4 to 6 bar and overflowed into a stirred collecting tank. The circulating pump delivered a circulating stream of about 11,000 l/h, which corresponded to a volume ratio of the circulating stream to the combined feed stream of about 100:1. It was then extracted with desalinated water in a four-stage countercurrent extractor. The bulk of the dichloromethane was first distilled off from the organic phase at 160 to 200 mbar in a thin-layer evaporator. Then, the N,N-diethylcyanamide, that was produced as by-product, and the residual content of dichloromethane and other volatile components were removed in a second thin-layer evaporator at 130° to 135° C. The novolac cyanate that accumulated as a bottom product was collected in a stirring vessel that was heated to 80° C. and, after the distillation was completed, it was decanted into casks under nitrogen.

EXAMPLE 3
Production of 4,4'-Ethylidenediphenylcyanate (Bisphenol-E-dicyanate)

Into a 15 l loop reactor that was cooled to an internal temperature of −7° to −3° C., 20 kg/h of a solution of 50 kg of 4,4'-ethylidenediphenol (bisphenol-E), that was precooled to −10° to −15° C., and 48.9 kg of triethylamine in 310 l of butyl acetate were introduced via a metering pump, and 3.4 kg/h of cyanogen chloride was simultaneously introduced via a control valve. The reaction mixture was circulated in the loop by a circulating pump at a pressure of 4 to 6 bar and overflowed into a stirred collecting tank. The circulating pump delivered a circulating stream of about 11,000 l/h, which corresponded to a volume ratio of the circulating stream to the combined feed stream of about 100:1. Then, it was extracted with desalinated water in a four-stage countercurrent extractor at 60° C. The bulk of the butyl acetate was first distilled off from the organic phase at 60 to 150 mbar in a thin-layer evaporator. Then, the N,N-diethylcyanamide, that was produced as by-product, and the residual content of butyl acetate and other volatile components were removed in a second thin-layer evaporator at 180° C. and 5 mbar. The bisphenol-E-dicyanate that accumulated as a bottom product was collected in a stirring vessel that was heated to 70° C. and, after the distillation was completed, it was decanted into casks under nitrogen.

EXAMPLE 4
Production of An Arylcyanate with Bridging Cycloaliphatic Groups

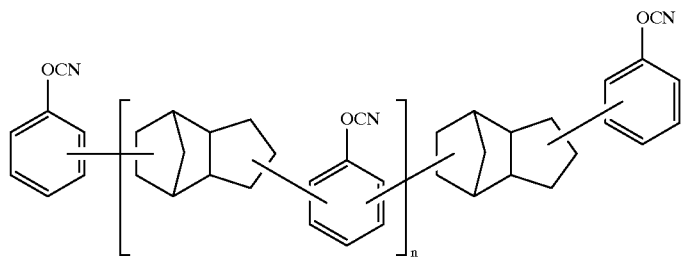

Into a 15 l loop reactor that was cooled to an internal temperature of −7° to −3° C., 80 l/h of a solution of 50 kg of polyphenol (Dow Chemical Co.) that was precooled to −10° to −15° C. and 33 kg of triethylamine in 310 l of butyl acetate were introduced via a metering pump, and 4.5 to 4.8 kg/h (22 to 24 kg in all) of cyanogen chloride was simultaneously introduced via a control valve. The reaction mixture was circulated in the loop by a circulating pump at a pressure of 4 to 6 bar and overflowed into a stirred collecting tank. The circulating pump delivered a circulating stream of about 11,000 l/h, which corresponded to a volume ratio of the circulating stream to the combined feed stream of about 100:1. Then, it was extracted with desalinated water in a four-stage countercurrent extractor of 60° to 70° C. The bulk of the butyl acetate was first distilled off from the organic phase at 70° C. and 60 to 150 mbar in a thin-layer evaporator. Then, the N,N-diethylcyanamide, that was produced as by-product, and the residual content of butyl acetate and other volatile components were removed in a second thin-layer evaporator at 180° C. and 5 mbar. The polycyanate that accumulated as a bottom product was collected in a stirring vessel that was heated to 70° C. and, after the distillation was completed, it was decanted into casks under nitrogen.

What is claimed is:

1. A process for the production of an aryl cyanate of formula I:

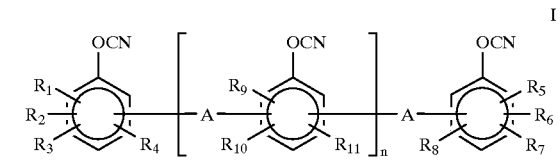

I wherein:

(a) n is a whole number from 0 to 20, and A is a direct bond, oxygen, sulfur, sulfonyl, carbonyl, carbonyldioxy, an optionally completely or partially fluorine-substituted, straight-chain or branched $C_1$–$C_{10}$-alkanediyl group, an optionally $C_1$–$C_4$-alkyl- and/or halogen-substituted, divalent monocyclic or polycyclic aromatic radical, an optionally $C_1$–$C_4$-alkyl-substituted, divalent monocyclic or polycyclic cycloaliphatic radical or a divalent group composed of two or more of the above-mentioned groups, and, if n is greater than zero, the groups respectively symbolized by A can be the same or different, or (b) n equals zero, A is a group of formula:

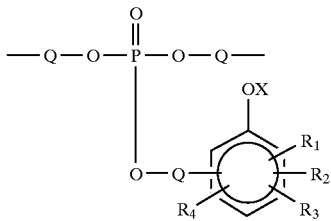

and Q is a direct bond, an optionally completely or partially fluorine-substituted, straight-chain or branched $C_1$–$C_{10}$-alkanediyl group, an optionally $C_1$–$C_4$-alkyl- and/or halogen-substituted, divalent monocyclic or polycyclic aromatic radical or a divalent group composed of two or more of the above-mentioned groups and X is —CN, and $R_1$ to $R_{11}$, are each the same or different and are hydrogen, halogen, $C_1$–$C_4$-alkoxy, $C_1$–$C_4$-alkylthio, $C_1$–$C_4$-alkoxycarbonyl or optionally completely or partially fluorine-substituted $C_1$–$C_4$alkyl, by reaction of a phenol of formula II:

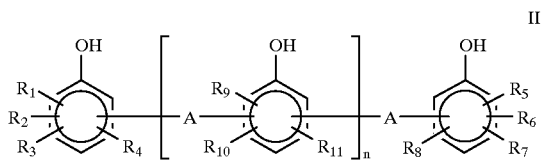

wherein n, A, Q and $R_1$ to $R_{11}$ have the above-mentioned meanings and X is hydrogen, with cyanogen chloride in the presence of a tertiary amine, characterized in that the phenol, the amine and the cyanogen chloride, of which at least one of the three components is present as a solution in an organic solvent, are fed essentially simultaneously and continuously at a temperature of –20° C. to 0° C. and in a molar ratio of cyanogen chloride to the reactive hydroxy groups of the phenol of 1.0:1.0 to 1.2:1.0 in a cooled loop reactor, so that the reaction components, before they come in contact with one another, are predilated by the reaction mixture circulating in the loop reactor, and simultaneously, a stream of the reaction mixture corresponding to the fed volume of the reaction components is drawn off from the circulation.

2. The process according to claim 1 wherein the molar ratio of cyanogen chloride to the reactive hydroxy groups of the phenol is from 1.0:1.0 to 1.1:1.0.

3. The process according to claim 2 wherein a trialkylamine of formula RR'R"N is used as the tertiary amine, wherein R, R' and R" are the same or different and each is a straight-chain or branched $C_1$–$C_6$-alkyl group.

4. The process according to claim 3 wherein triethylamine is used as the tertiary amine.

5. The process according to claim 4 wherein an organic solvent is used, in which the resulting tertiary ammonium chloride is poorly soluble.

6. The process according to claim 5 wherein the tertiary ammonium chloride is separated completely or partially from the reaction mixture by filtration or centrifuging.

7. The process according to claim 6 wherein a solvent is used, which is not water-miscible and the reaction mixture, optionally after filtration or centrifuging, is extracted with water.

8. The process according to claim 1 wherein a trialkylamine of formula RR'R"N is used as the tertiary amine, in which R, R' and R" are the same or different and each is a straight-chain or branched $C_1$–$C_6$-alkyl group.

9. The process according to claim 8 wherein triethylamine is used as the tertiary amine.

10. The process according to claim 1 wherein an organic solvent is used, in which the resulting tertiary ammonium chloride is poorly soluble.

11. The process according to claim 10 wherein the tertiary ammonium chloride is separated completely or partially from the reaction mixture by filtration or centrifuging.

12. The process according to claim 1 wherein a solvent is used, which is not water-miscible and the reaction mixture, optionally after filtration or centrifuging, is extracted with water.

13. The process according to claim 1 wherein the volume ratio of the circulating stream in the loop reactor to the combined feed stream of the reaction components is equal to or greater than 10 to 1.

14. The process according to claim 1 wherein the volume ratio of the circulating stream in the loop reactor to the combined feed stream of the reaction components is equal to or greater than 100 to 1.

15. The process according to claim 1 wherein only the phenol is used as a solution in an organic solvent, and the three components are fed at a temperature of –6° C. to 0° C.

16. The process according to claim 1 wherein the organic solvent is ethyl acetate, butyl acetate, tetrahydrofuran, acetone or dichloromethane.

17. The process according to claim 1 wherein the phenol of formula II is a multivalent phenol of formula II, and A in the phenol of formula II is selected from the group consisting of oxygen, sulfur, sulfonyl, carbonyl and carbonyldioxy.

18. A process for the production of an aryl cyanate of formula I:

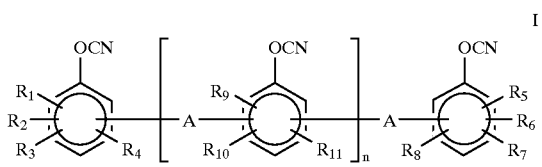

wherein:

(a) n is a whole number from 0 to 20, and A is a direct bond, oxygen, sulfur, sulfonyl, carbonyl, carbonyldioxy, an optionally completely or partially fluorine-substituted, straight-chain or branched $C_1$–$C_{10}$-alkanediyl group, an optionally $C_1$–$C_4$-alkyl- and/or halogen-substituted, divalent monocyclic or polycyclic aromatic radical, an optionally $C_1$–$C_4$-alkyl-substituted, divalent monocyclic or polycyclic cycloaliphatic radical or a divalent group composed of two or more of the above-mentioned groups, and, if n is greater than zero, the groups respectively symbolized by A can be the same or different, or (b) n equals zero, A is a group of formula:

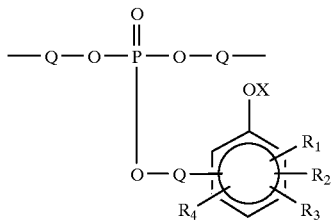

and Q is a direct bond, an optionally completely or partially fluorine-substituted, straight-chain or branched $C_1$–$C_{10}$-alkanediyl group, an optionally $C_1$–$C_4$-alkyl- and/or halogen-substituted, divalent monocyclic or polycyclic aromatic radical or a divalent group composed of two or more of the above-mentioned groups and X is —CN, and $R_1$ to $R_{11}$ are each the same or different and are hydrogen, halogen, $C_1$–$C_4$-alkoxy, $C_1$–$C_4$alkylthio, $C_1$–$C_4$-alkoxycarbonyl or optionally completely or partially fluorine-substituted $C_1$–$C_4$alkyl, by reaction of a phenol of formula II:

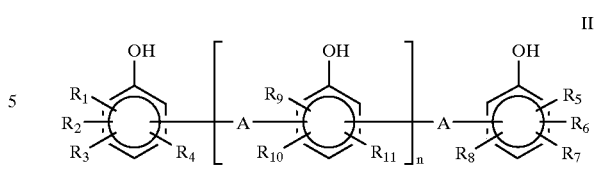

wherein n, A, Q and $R_1$ to $R_{11}$ have the above-mentioned meanings and X is hydrogen, with cyanogen chloride in the presence of a tertiary amine, characterized in that the phenol, the amine and the cyanogen chloride, of which at least one of the three components is present as a solution in an organic solvent, are fed essentially simultaneously and continuously at a temperature of −20° C. to 0° C. and in a molar excess of cyanogen chloride to the reactive hydroxy groups of the phenol in a cooled loop reactor, so that the reaction components, before they come in contact with one another, are pre-diluted by the reaction mixture circulating in the loop reactor, and simultaneously, a stream of the reaction mixture corresponding to the fed volume of the reaction components is drawn off from the circulation.

* * * * *